(12) United States Patent
Terakawa

(10) Patent No.: US 7,970,578 B2
(45) Date of Patent: Jun. 28, 2011

(54) COMPENSATION TABLE GENERATION METHOD, APPARATUS AND COMPUTER PROGRAM PRODUCT, AND TOMOGRAPHY IMAGE PROCESSING APPARATUS USING THE SAME

(75) Inventor: Kensuke Terakawa, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 372 days.

(21) Appl. No.: 12/114,152

(22) Filed: May 2, 2008

(65) Prior Publication Data

US 2009/0244546 A1 Oct. 1, 2009

(30) Foreign Application Priority Data

May 2, 2007 (JP) ................................. 2007-121472

(51) Int. Cl.
*G01B 5/02* (2006.01)
(52) U.S. Cl. ........ 702/159; 702/155; 702/156; 702/189; 702/190; 702/198; 702/19; 702/66; 356/497
(58) Field of Classification Search .................... 702/159
See application file for complete search history.

(56) References Cited

U.S. PATENT DOCUMENTS

| 5,956,355 A * | 9/1999 | Swanson et al. ................ 372/20 |
| 2006/0034418 A1 * | 2/2006 | Heismann et al. ................ 378/4 |

OTHER PUBLICATIONS

Yoshiaki Yasuno et al, "Three-dimensional and high speed swept-source optical coherence tomography for in vivo investigation of human anterior eye segments", Optics Express, Dec. 26, 2005, vol. 13, No. 26, pp. 10652-10664.

* cited by examiner

*Primary Examiner* — Drew A Dunn
*Assistant Examiner* — Hyun Park
(74) *Attorney, Agent, or Firm* — Sughrue Mion, PLLC

(57) ABSTRACT

A compensation table for compensating interference signal obtained by OCT measurement is generated easily. When a reflection body interference signal is obtained by OCT measurement, the reflection body interference signal is compensated by a compensation table (Formula (1)) to obtain an evaluation output signal. Then, a spectrum of the evaluation output signal is calculated to obtain an evaluation value of the spectrum. Thereafter, a model coefficient is updated such that the evaluation value becomes small.

14 Claims, 8 Drawing Sheets

COMPENSATION TABLE GENERATION METHOD, APPARATUS AND COMPUTER PROGRAM PRODUCT, AND TOMOGRAPHY IMAGE PROCESSING APPARATUS USING THE SAME

BACKGROUND OF THE INVENTION

1. Field of the Invention

The present invention relates to a compensation table generation method, apparatus and computer program product for generating a compensation table used when generating an optical tomography image by OCT (Optical Coherence Tomography) measurement. The invention also relates to a tomography image processing apparatus using the same.

2. Description of the Related Art

The use of optical tomography image obtaining systems employing OCT measurement is proposed when obtaining optical tomography images of living tissues. Such systems are applied to the observation of various regions ranging from fundus or anterior chamber of an eye, or skin to the observation of an artery wall using a fiber probe or of a digestive organ using a fiber probe inserted through the forceps channel of an endoscope. In the optical tomography image obtaining system, low coherence light emitted from a light source is split into measuring light and reference light, then reflection light or backscattered light from a measuring object when the measuring light is irradiated on the measuring object is combined with the reference light, and an optical tomography image is obtained based on the intensity of interference light between the reflection light and the reference light. Hereinafter, reflection light and backscattered light from a measuring object are collectively referred to as the "reflection light".

The OCT measurement is largely grouped into TD-OCT (Time Domain OCT) measurement and FD (Fourier Domain)-OCT measurement. The TD-OCT measurement is a method for obtaining a reflection light intensity distribution corresponding to a position in the depth direction (depth position) of a measuring object by measuring interference light intensity while changing the optical path length of the reference light.

The FD-OCT measurement is a method for obtaining a reflection light intensity distribution corresponding to a depth position of a measuring object by measuring interference light intensity with respect to each spectral component of the light without changing the optical path length of the reference light, and performing frequency analysis, typically a Fourier transform, on the obtained spectral interference intensity signals using a computer. The FD-OCT does not require the mechanical scanning used in TD-OCT, so that it has been drawing wide attention as a method that allows high speed measurement. Typical systems that use FD-OCT measurement are SD-OCT (Spectral Domain OCT) system and SS-OCT (Swept Source OCT) system as described, for example, in U.S. Pat. No. 5,956,355 (Patent Document 1), and a non-patent document "Three-dimensional and high-speed swept-source optical coherence tomography for in vivo investigation of human anterior eye segments" by Yoshiaki Yasuno et al., OPTICS EXPRESS, Vol. 13, No. 26, pp. 10652-10664, 2005 (Non-Patent Document 1).

Here, in the FD-OCT measurement, a detected interference signal represents interference intensity with respect to wavelength, while an interference signal representing interference intensity with respect to wave number is required in the frequency analysis for obtaining tomography information from the interference signal. Consequently, in the Non-Patent Document 1, wavelength sweep characteristic is calculated from an interference signal obtained with a mirror as the sample, and the interference signal obtained as interference intensity with respect to each wavelength is converted to an interference signal representing interference intensity with respect to each wave number based on the calculated wavelength sweep characteristic. In the Patent Document 1, information of wavelength sweep characteristic of the light source with respect to time is obtained in advance. Then, based on the timing when an interference signal is observed and the wavelength sweep characteristic, the interference signal is converted to an interference signal with respect to wave number, which is further converted such that the interference intensities are evenly spaced apart with respect to a wave number k.

Provision of a conversion table by measuring wavelength sweep characteristic of light in advance, as in the Patent Document 1 and Non-Patent Document 1, however, causes a problem that it takes time and effort. Consequently, it has been anticipated that the conversion table be created more easily.

In view of the circumstances described above, it is an object of the present invention to provide a compensation table generation method, apparatus and computer program product capable of generating a compensation table used for data conversion of an interference signal obtained by OCT measurement more easily. It is a further object of the present invention to provide a tomography image processing apparatus using the same.

SUMMARY OF THE INVENTION

The compensation table generation method of the present invention is a method for generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the method including the steps of:

obtaining an interference signal sampled when a reflection body is disposed in the optical axis directions of the measuring light as a reflection body interference signal;

calculating an evaluation output signal by resampling the obtained reflection body interference signal in a sampling space converted by Formula (1) below; and optimizing a model coefficient of a compensation table set as a N-order polynomial in Formula (1) below using the calculated evaluation output signal.

$$y = \sum_{i=1}^{N-1} c_i x^{N+1-i} + \left(1 - \sum_{i=1}^{N-1} c_i\right) x \quad (1)$$

x is the reflection body interference signal sampling space
y is the evaluation output signal sampling space
$c_i$ is the model coefficient (i=1, 2, ..., N−1)

The compensation table generation apparatus of the present invention is an apparatus for generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the apparatus including:

an interference signal obtaining means for obtaining an interference signal sampled when a reflection body is disposed in the optical axis directions of the measuring light as a reflection body interference signal;

an evaluation signal calculation means for calculating an evaluation output signal by resampling the reflection body interference signal obtained in the interference signal obtaining means in a sampling space converted by Formula (1) above; and an optimization means for optimizing a model coefficient of a compensation table set as a N-order polynomial in Formula (1) above using the evaluation output signal calculated by the evaluation signal calculation means.

The compensation table generation computer program product of the present invention is a computer program product for generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the computer program product causing a computer to perform the steps of:

obtaining an interference signal sampled when a reflection body is disposed in the optical axis directions of the measuring light as a reflection body interference signal;

calculating an evaluation output signal by resampling the obtained reflection body interference signal in a sampling space converted by Formula (1) above; and optimizing a model coefficient of a compensation table set as a N-order polynomial in Formula (1) above, using the calculated evaluation output signal.

The tomography image processing apparatus of the present invention is an apparatus for generating a tomography image of a measuring object by emitting light, splitting the emitted light into measuring light and reference light, combining reflection light from the measuring object when the measuring light is irradiated on the measuring object with the reference light, sampling interference light when the reflection light is combined with the reference light as an interference signal, and obtaining tomography information of the measuring object using the sampled interference signal, the apparatus including:

an interference signal obtaining means for obtaining an interference signal;

an evaluation signal calculation means for calculating an evaluation output signal by resampling a reflection body interference signal, which is a portion of the interference signal obtained in the interference signal obtaining means, in a sampling space converted by Formula (1) above;

an optimization means for optimizing a model coefficient of a compensation table set as a N-order polynomial in Formula (1) above, using the evaluation output signal calculated by the evaluation signal calculation means;

a signal compensation means for compensating the interference signal obtained in the interference signal obtaining means using the compensation table optimized by the optimization means;

a tomography information obtaining means for obtaining tomography information of the measuring object using the interference signal compensated by the signal compensation means; and a tomography image generation means for generating a tomography image using the tomography information obtained by the tomography information obtaining means.

The term "reflection light" as used herein means reflection light and backscattered light.

Further, the term "reflection body" as used herein means a test sample having an extraordinary high reflectance. For example, where measuring light is guided through an optical probe having an optical fiber covered by a sheath and irradiated on a measuring object transmitted through the sheath, the sheath may be used as the reflection body, or otherwise a mirror or the like may be used.

The interference signal obtaining means may be any means if it is capable of obtaining interference signal sampled when a reflection body is disposed in the optical directions of the measuring light as a reflection body interference signal. It may be a means for obtaining a reflection body interference signal whose sampling space is the wavelength of interference light. Here, the evaluation signal calculation means may be a means for calculating an evaluation output signal whose sampling space is the wave number of the interference light by resampling the reflection body interference signal in the sampling space converted by Formula (1) above.

Alternatively, the interference signal obtaining means may be a means having a function to covert a reflection body interference signal representing the interference intensity with respect to the wavelength of the interference light to a reflection body interference signal representing the interference intensity with respect to the wave number of the interference light. Here, the evaluation signal calculation means may be a means for calculating an evaluation output signal by resampling the reflection body interference signal representing the interference intensity with respect to the wave number obtained by the interference signal obtaining means in the sampling space converted by Formula (1) above.

The initial value of the model coefficient $C_i$ in Formula (1) above may be an appropriate value substituted thereto, or it may be obtained from an already existing compensation table.

Further, the reflection body interference signal may be any interference signal if it is obtained by sampling while a reflection body is disposed in the optical axis directions of the measuring light, but it is preferable that the reflection body interference signal is an interference signal obtained while only the reflection body is disposed.

Still further, in Formula (1) above, the order number N and the norm M may be set to any values, but it is preferable that the norm M is set to a value from 1 to less than 2 to make the spectrum to be a sparse signal.

Further, the optimization means may be any means if it is capable of optimizing the model coefficient. For example, the optimization may be performed by simplex method or Powell method. More specifically, the optimization means may be a means that includes a spectrum calculation means for calculating a spectrum of the evaluation output signal obtained in the evaluation signal calculation means, an evaluation value calculation means for calculating an evaluation value for the compensation table by Formula (2) below using the spectrum calculated in the spectrum calculation means; and a coefficient updating means for updating the model coefficient such that the evaluation value calculated by the evaluation value calculation means becomes small.

$$E(c_i) = \sum_t |Y(t)|^M \quad (2)$$

$E(c_i)$ is the evaluation value for the compensation table of formula (1) above Y(t) is the spectrum of the evaluation output signal
M is the set norm set such that the signal component from the reflection body and signal component other than from the reflection body become sparse signals in the spectrum Y(t)

Still further, the tomography information obtaining means may be any means if it is capable of obtaining tomography information at each depth position from the interference signal. For example, the tomography information may be obtained through spectrum analysis by Fourier transform, maximum entropy method, Yule-Walker method, and the like.

Further, the light may be light emitted while the wavelength is periodically swept within a predetermined wavelength range and used in so-called SS-OCT measurement for obtaining a tomography image, or low coherence light having a predetermined wavelength range and used in so-called SD-OCT measurement for obtaining a tomography image.

According to the method, apparatus, and computer program product for generating a compensation table of the present invention, and the tomography image processing apparatus using the same, when generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the following is performed. That is, obtaining an interference signal sampled when a reflection body is disposed in the optical axis directions of the measuring light as a reflection body interference signal, calculating an evaluation output signal by resampling the obtained reflection body interference signal in a sampling space converted by Formula (1) above; and optimizing a model coefficient of a compensation table set as a N-order polynomial in Formula (1) above using the calculated evaluation output signal. This eliminates the need for measuring the wavelength sweeping characteristics of the light source unit in advance for generating a compensation table as required in the conventional techniques. Instead, by making use of the fact that a reflection body interference signal from the reflection body and an interference signal other than the reflection body interference signal become sparse signals, the compensation table may be generated easily.

If the optimization means includes a spectrum calculation means for calculating a spectrum of the evaluation output signal obtained in the evaluation signal calculation means, an evaluation value calculation means for calculating an evaluation value for the compensation table by Formula (2) above using the spectrum calculated in the spectrum calculation means, and a coefficient updating means for updating the model coefficient such that the evaluation value calculated by the evaluation value calculation means becomes small, the compensation table may be generated automatically and efficiently.

If the interference signal obtaining means is a means having a function to convert a reflection body interference signal sampled as the interference intensity with respect to the wavelength to a reflection body interference signal representing the interference intensity with respect to the wave number, and the optimization means is a means for optimizing a compensation table model coefficient using the evaluation output signal calculated by the evaluation signal calculation means, the already converted to interference signal representing the interference intensity with respect to the wave number may be finely adjusted, thereby image quality is improved.

Further, if the measuring light is light guided through an optical probe having an optical fiber covered by a sheath and irradiated on the measuring object transmitted through the sheath, and the reflection body is the sheath, a separate reflection body for obtaining the reflection body interference signal needs not be provided in the optical axis directions of the measuring light, so that the compensation table may be generated more easily.

DESCRIPTION OF THE PREFERRED EMBODIMENTS

Figure 1:
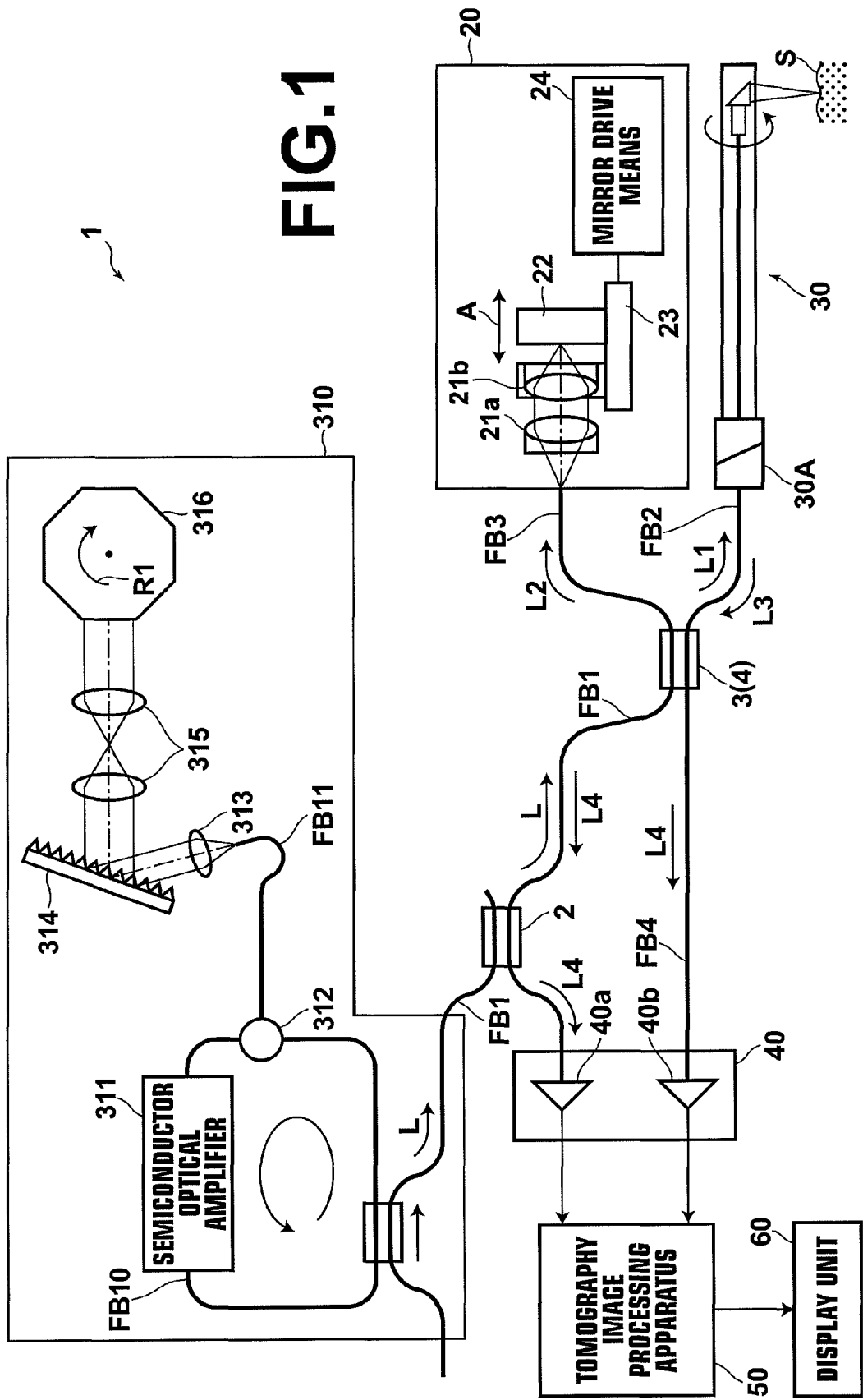
FIG. 1 is a schematic configuration diagram of an exemplary embodiment of the optical tomography system to which a compensation table generation apparatus of the present invention is applied.

Herein after an embodiment of the tomography image processing apparatus of the present invention will be described in detail with reference to the accompanying drawings. FIG. 1 is a schematic view of an exemplary embodiment of an optical tomography system using the tomography image processing apparatus of the present invention. The optical tomography apparatus 1 shown in FIG. 1 is an apparatus for obtaining a tomography image P of a measuring object, such as a living tissue, a cell, and the like in a body cavity by SS-OCT measurement. The optical tomography apparatus 1 includes: a light source unit 310 that outputs light L; a light splitting means 3 that splits the light L outputted from the light source unit 310 into measuring light L1 and reference light L2; a light combining means 4 that combines reflection light (backscattered light) when the measuring light is reflected at each depth position of a measuring object S with the reference light L2; an interference light detection means 40 that samples interference light L4 between the reflection light L3 and reference light L2 combined by the light combining means 4 as an interference signal IS; and a tomography image processing apparatus 50 that generates a tomography image from the interference signal sampled by the interference light detection means 40.

Figure 2:
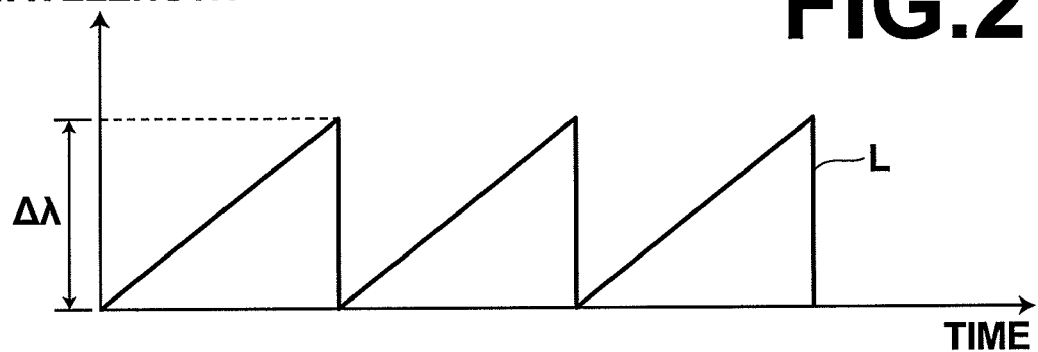
FIG. 2 is a graph illustrating how the wavelength of light emitted from the light source unit shown in FIG. 1 is swept.

The light source unit 310 is a unit that outputs the laser light L while sweeping the wavelength thereof within a wavelength range Δλ shown in FIG. 2 at a constant period T. More specifically, the light source unit 310 includes a semiconductor optical amplifier (semiconductor gain medium) 311 and an optical fiber FB10, which is connected to each end of the semiconductor optical amplifier 311. The semiconductor optical amplifier 311 has functions to output a weak emission light to one end of the optical fiber FB10 when a drive current is injected and to amplify light inputted from the other end of the optical fiber FB10. When the drive current is supplied to the semiconductor optical amplifier 311, pulse laser light L is outputted to an optical fiber FB1 by the optical resonator formed of the semiconductor optical amplifier 311 and optical fiber FB10.

Further, an optical brancher 312 is connected to the optical fiber FB10, and a portion of light guided through the optical fiber FB10 is outputted to an optical fiber FB11 from the optical brancher 312. The light outputted from the optical fiber FB11 is passed through a collimator lens 313, a diffraction grating element 314, and an optical system 315, and then reflected by a rotational polygon mirror 316. The reflected light is inputted back to the optical fiber FB11 again through the optical system 315, diffraction grating element 314, and collimator lens 313.

Here, the rotational polygon mirror 316 is designed to rotate in the arrow R1 direction and the angle of each reflection surface is changed with respect to the optical axis of the optical system 315. This causes only the light having a wavelength in a particular wavelength range of the light dispersed by the diffraction grating element 314 to be returned to the optical fiber FB11. The wavelength of the light returned to the optical fiber FB11 is dependent on the angle between the optical axis of the optical system 315 and the reflection surface. The light having wavelengths within the particular wavelength range and inputted to the optical fiber FB11 is inputted back to the optical fiber FB10 from the optical brancher 312. As a result, laser light L having wavelengths within the particular wavelength range is outputted to the optical fiber FB1.

Accordingly, when the rotational polygon mirror 316 is rotated in the arrow R1 direction at a constant speed, the wavelength λ of the light inputted back to the optical fiber FB11 will be changed with time at a constant period. In this way, laser light L wavelength-swept at a constant period T and having a spectrum intensity shown in FIG. 2 is outputted from the light source unit 310 to the optical fiber FB1.

The light splitting means 3 is formed of, for example, a 2×2 optical coupler, and splits the light L outputted from the light source unit 310 and guided through the optical fiber FB1 into the measuring light L1 and reference light L2. The light splitting means 3 is optically coupled to two optical fibers FB2 and FB3, and the measuring light L1 is guided through the optical fiber FB2, and the reference light L2 is guided through the optical fiber FB3. It is noted that the light splitting means 3 in the present embodiment functions also as the light combining means 4.

Figure 3:
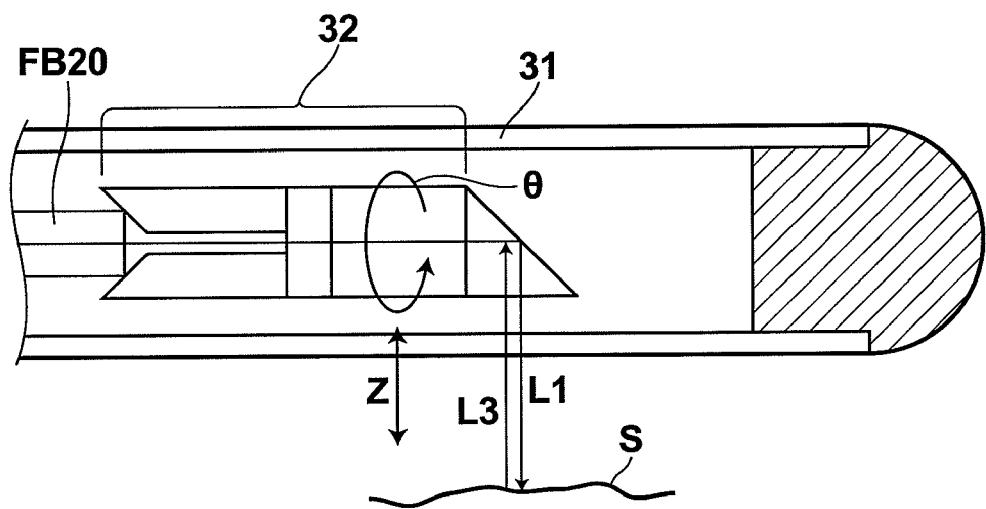
FIG. 3 is a schematic view of an example optical probe used in the optical tomography system shown in FIG. 1.

An optical probe 30 is optically coupled to the optical fiber FB2 and the measuring light L1 is guided from the optical fiber FB2 to the optical probe 30. FIG. 3 is a schematic view of the optical probe 30 shown in FIG. 1, illustrating an example distal end portion thereof. The optical probe 30 is inserted, for example, from a forceps inlet opening to a body cavity through the forceps channel, and removably attached to the optical fiber FB2 by an optical connector 30A. The optical probe 30 includes a sheath 31, an optical fiber FB20, an optical lens 32, and the like. The sheath 31 is a cylindrical member having flexibility made of a material which is transparent to the measuring light L and the reference light L2. The sheath 31 is closed at the tip by a cap.

The optical fiber FB20, accommodated inside the sheath 31, guides the measuring light L1 to a measuring object S, and guides reflection light L3 (backscattered light) from the measuring object S when the measuring light L1 is irradiated on the measuring object S to the optical fiber FB2. The optical fiber 20 is rotated in the arrow θ direction with respect to the sheath 31 by the optical connector 30A.

The optical lens 32 focuses the measuring light L1 outputted from the optical fiber FB20 on the measuring object S, and inputs reflection light L3 from the measuring object S to the optical fiber FB20 by focusing the reflection light L3 on the optical fiber FB20. The optical lens 32 fixed to a light output end of the optical fiber FB20, and when the optical fiber FB20 is rotated in the arrow θ direction, the optical lens 32 is also rotated in the arrow θ direction in an integrated manner. Accordingly, the optical probe 30 irradiates the measuring light L1 outputted from the optical lens 32 on the measuring object S while scanning the measuring light L1 in the arrow θ direction with respect to the measuring object S.

In the mean time, an optical path length adjustment means 20 is disposed on the reference light L2 output side of the optical fiber FB3. The optical path length adjustment means 20 is provided for changing the optical path length of the reference light L2 in order to adjusting the measuring start position for the measuring object S and includes a collimator lens 21 and reflection mirror 22. The reference light L2 outputted from the optical fiber FB2 is passed through the collimator lens 21 and reflected back by the reflection mirror 22, and inputted back to the optical fiber FB3 through the collimator lens 21.

Here, the reflection mirror 22 is disposed on a movable stage 23 which is movably provided in the arrow A directions by the mirror drive means 24. The optical path length of the reference light L2 is changed by moving the movable stage 23 in the arrow A directions.

The light combining means 4 is formed of a 2×2 optical coupler, and combines the reference light L2 adjusted in the optical path length thereof by the optical path length adjustment means 20 with the reflection light L3 from the measuring object S. At the same time, the light combining means 4 divides the combined light into halves and outputs the halved combined light to the interference light detection means 40 through the optical fiber FB1 and FB4 respectively.

The interference light detection means 40 is formed of, for example, a photodiode or the like. It samples the interference light between the reflection light L3 and the reference light L2 combined by the light combining means 4 and outputs the sampled interference light as an interference signal IS. In the present example apparatus, the halved interference light L4 divided by the light combining means (optical fiber coupler) 4 is guided to light detectors 40a and 40b respectively to perform balance detection.

An example operation of the optical tomography system 1 will now be described. First, the optical path length of the reference light L2 is adjusted by moving the moving stage 23 in the arrow A directions in order to bring a measuring object S into a measurable range. Then, light L is outputted from a light source unit 310, and the light L is split into measuring light L1 and reference light L2 by the light splitting means 3. The measuring light L1 is guided by the optical probe 30 to a body cavity and irradiated on the measuring object S. Then, reflection light L3 from the measuring object S is combined with the reference light L2, reflected by the reflection mirror 22, by the light combining means 4. Then interference light L4 between the reflection light L3 and the reference light L2 is sampled by the interference detection means 40 as an interference signal IS.

Thereafter, the optical fiber in the optical probe 30 is rotated in the arrow θ direction to scan the measuring light L1 in the arrow θ direction with respect to the measuring object S. Then, information of the measuring object S in the depth direction (optical axis direction z of the measuring light) at each point along the scanning direction θ is obtained. Thus, a tomography image P is obtained from the plurality of interference signals IS in the tomography image processing unit 50. It is also possible to scan the measuring light L1 with respect to the measuring object S in a second direction (longitudinal direction of the optical probe) which is orthogonal to the scanning direction described above to obtain a tomography image P of a cross-section that includes the second direction.

Figure 4:
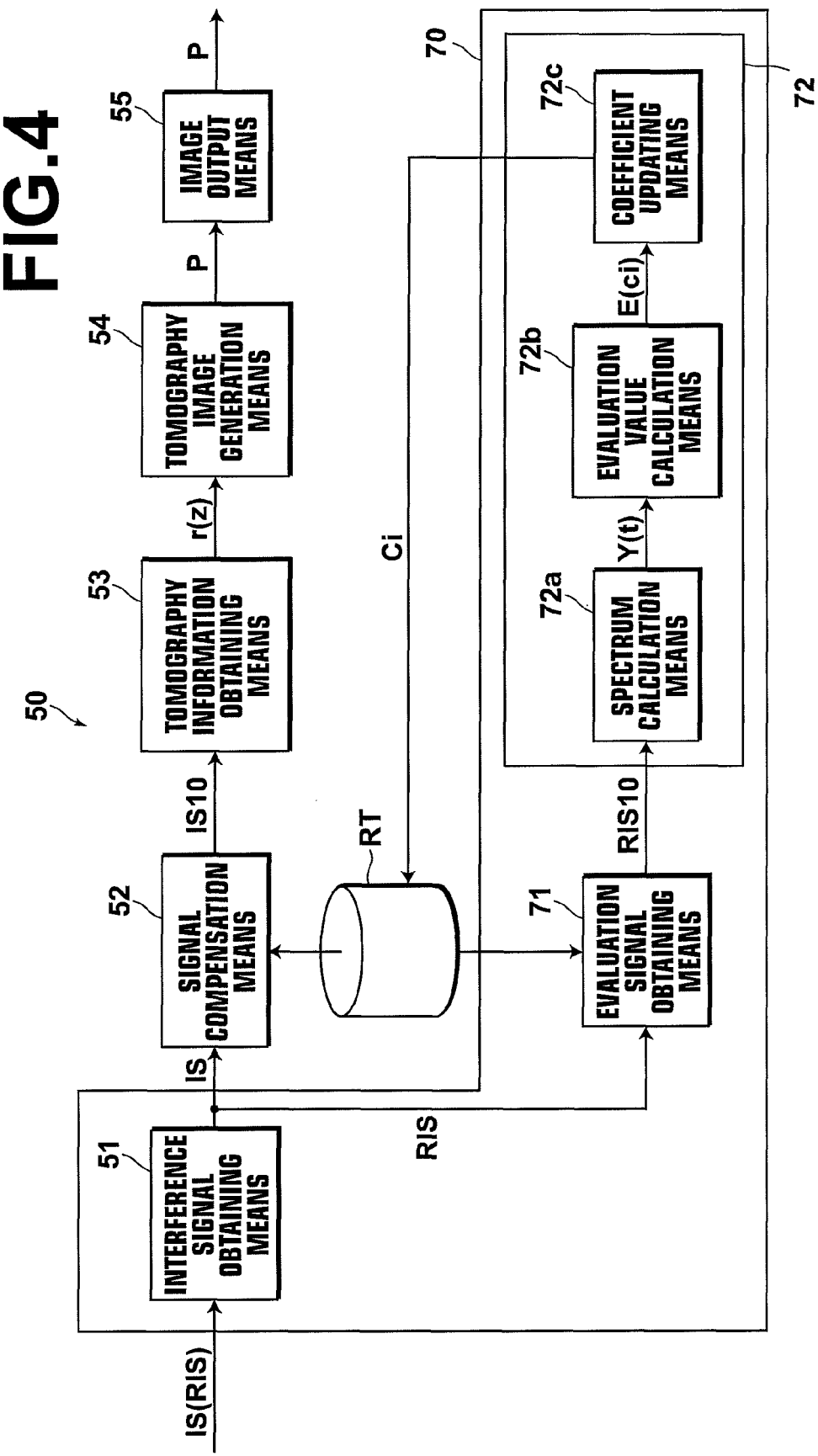
FIG. 4 is a block diagram of an exemplary embodiment of the tomography image processing apparatus of the present invention.

FIG. 4 is a block diagram of an exemplary embodiment of the tomography image processing apparatus of the present invention, and the tomography image processing apparatus 50 will now be described with reference to FIG. 4. It is noted that the configuration of the tomography image processing apparatus 50 shown in FIG. 4 is realized by executing a tomography image processing program, read into an auxiliary storage device, on a computer (e.g., personal computer). Here, the tomography image processing program is stored in an information storage medium, such as a CD-ROM or the like, or distributed through a network, such as the Internet or the like, and installed on the computer.

The tomography image processing apparatus 50 includes: an interference signal obtaining means 51; a signal compensation means 52; a tomography information obtaining means 53; a tomography image generation means 54; and an image output means 55. The interference signal obtaining means 51 is a means that obtains interference signals sampled in the interference light detection means 40. In the interference light detection means 40, interference signals are sampled under the influence of the spectrum intensity of the light L. Therefore, the interference signal obtaining means 51 may be constructed to perform preprocessing on the interference signals IS to remove the influence of the spectrum intensity of the light L.

Figure 5:
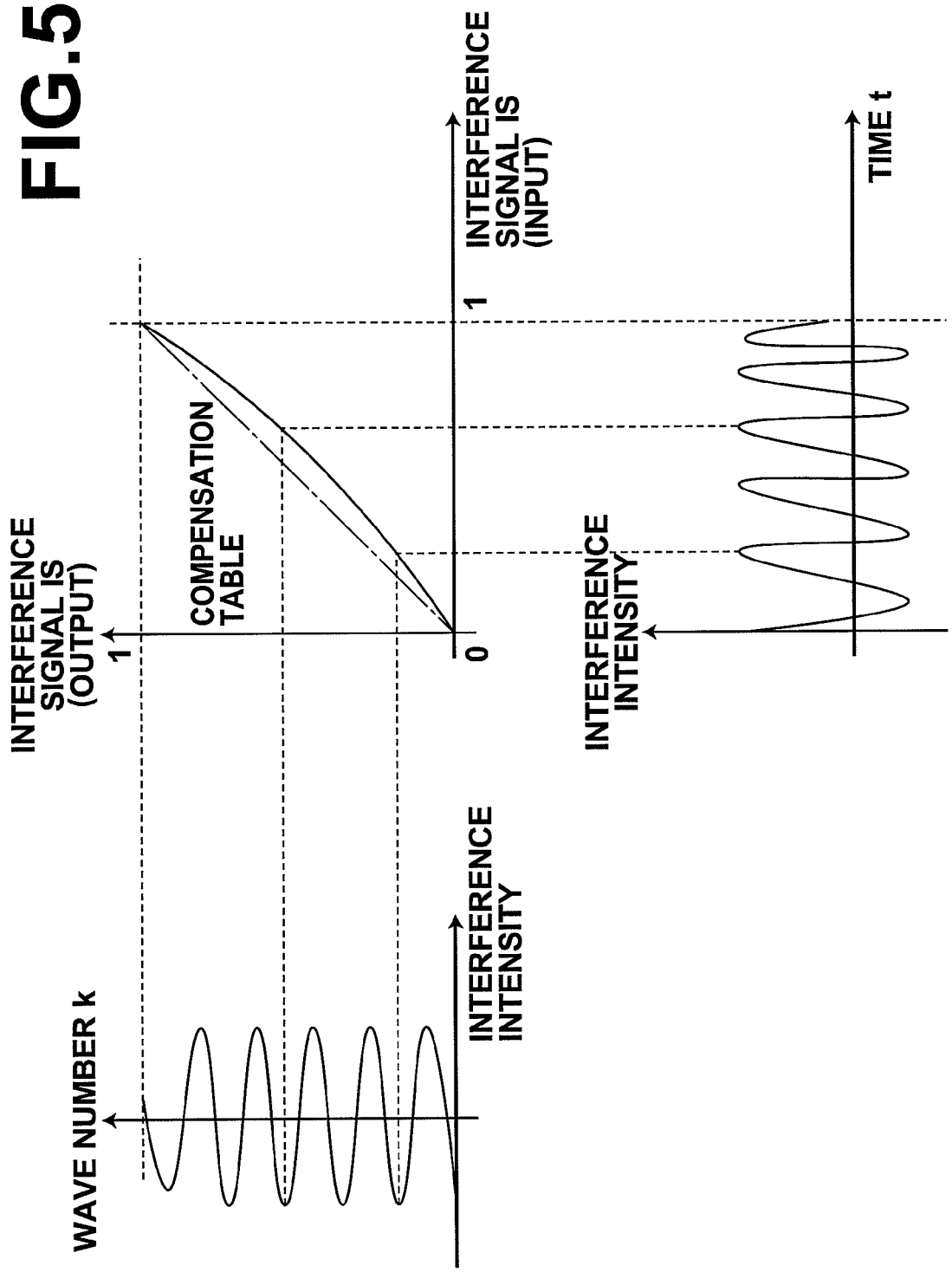
FIG. 5 is a schematic view illustrating how an interference signal is converted in the signal compensation means shown in FIG. 1.

The signal compensation means 52 shown in FIG. 3 compensates an interference signal IS using a compensation table represented by Formula (1) shown below and outputs the compensated interference signal IS10. As illustrated in FIG. 5, the signal compensation means 52 has functions to compensate (interpolate) an interference signal IS obtained as an interference intensity with respect to each wavelength (with respect to time elapsed) in the interference light detection means 40 and to generate an compensated interference signal IS10 with interference intensities arranged evenly spaced apart on the axis of wave number k (=2π/λ).

$$y = \sum_{i=1}^{N-1} c_i x^{N+1-i} + \left(1 - \sum_{i=1}^{N-1} c_i\right) x \quad (1)$$

x is the reflection body interference signal sampling space
y is the evaluation output signal sampling space
$c_i$ is the model coefficient (i=1, 2, ..., N−1)

That is, the interference light detection means 40 samples interference intensities as an interference signal IS when the sampling space is the change in time (change in wavelength λ). Meanwhile, the signal compensation means 52 resamples the interference signal IS to interference intensities when the sampling space is the wave number k (2π/λ) and generates a compensated interference signal IS10. A compensation table RT is a table that indicates which resampling point y in the resampling space in wave number corresponds to a sampling point x in the sampling space in wavelength when the sampling space conversion described above is performed.

The sampling space x is an integer, but the resampling point y derived from Formula (1) is not always an integer. In such a case, the signal compensation means 52 uses the interference intensity at the resampling point y with a decimal point to interpolate the interference intensity at the integer resampling point y, and generates a compensated interference signal IS10. The signal conversion method is disclosed in detail in U.S. Pat. No. 5,956,355.

The tomography information obtaining means 53 obtains tomography information r(z) at each depth position of a measuring object S using the compensated interference signal IS10. Here, the tomography information obtaining means 53 obtains tomography information (reflectance) in the depth direction z using one of the known spectrum analysis techniques, such as the Fourier transform, maximum entropy method (MEM), Yule-Walker method, and the like. Further, the tomography information obtaining means 53 obtains tomography information r(z) for one line every time a portion of the interference signal IS corresponding to one period of wavelength sweeping is sampled in the interference light detection means 40.

The tomography image generation means 54 generates a single tomography image from tomography information for a plurality of lines serially obtained by the tomography information obtaining means 53. More specifically, the tomography image generation means 54 stores tomography information r(z) obtained from a portion of the interference signal IS corresponding to one period of wavelength sweeping in the light source unit 310 shown in FIG. 1 as tomography information r(z) for one line. Further, when the measuring light L1 is irradiated on the measuring object S while scanned with respect to the measuring object S, the tomography image generation means 54 stores a plurality of sets of tomography information r (z) serially obtained. Thereafter, the tomography image generation means 54 generates a tomography image P using the tomography information r (z) for a plurality of lines stored therein. Then, the tomography image P generated by the tomography image generation means 54 is displayed on a display unit 60 shown in FIG. 1 by the image output means 55.

Here, the compensation table RT used in the signal compensation means 52 is a table generated by a compensation table generation unit 70 shown in FIG. 4. It is noted that the configuration of the compensation table generation unit 70 is realized by executing a compensation table generation program, read into an auxiliary storage device, on a computer (e.g., personal computer). Here, the compensation table generation program is stored in an information storage medium, such as a CD-ROM or the like, or distributed through a network, such as the Internet or the like, and installed on the computer.

The compensation table generation unit 70 includes: the interference signal obtaining means 51; an evaluation signal obtaining means 71; and an optimization means 72. The interference signal obtaining means 51 has a function to obtain an interference signal obtainable when a reflection body (the sheath 31) is disposed in the optical directions of the measuring light L1 (the arrow z directions in FIG. 3) as a reflection body interference signal RIS, not just to obtain the interference signal IS when the interference light L4 between the reflection light L3 from the measuring object S and the reference light L2 is sampled as described above. For example, the interference signal obtaining means 51 obtains an interference signal sampled when the measuring light L1 is outputted from the optical probe 30 without inserting the optical probe 30 into a body cavity and without reflection light L3 from a measuring object S as the reflection body interference signal RIS.

The evaluation signal obtaining means 71 calculates a reflection interference signal by resampling the reflection body interference signal RIS using Formula (1) above as an evaluation output signal RIS10, and has functions identical to those of the signal compensation means 52 described above.

The evaluation signal obtaining means 71 has appropriate initial values for the number of dimensions N and model coefficient $C_i$ in Formula (1) above, which have been determined regarding the fact that the wave number $k=2\pi/\lambda$. For example, if the number of dimensions N is set to four (N=4), the initial compensation table RT is like Formula (1') below, and the initial value of the model coefficient $C_i$ (i=1, 2, 3) in Formula (1) is preset to an appropriate value.

$$y = c_1 x^4 + c_2 x^3 + c_3 x^2 + (1-c_1-c_2-c_3)x \qquad (1')$$

Then, the evaluation signal obtaining means 71 obtains the interference intensity at a resampling point y from the interference intensity at a sampling point x in Formula (1') to obtain the evaluation output signal RIS10.

The optimization means 72 optimizes the model coefficient $C_i$ represented by Formula (1) above using the reflection body interference signal RIS obtained in the interference signal obtaining means 51. Here, the optimization means 72 performs the optimization of the model coefficient $C_i$ using the simplex method, Powell method, or the like. It includes a spectrum calculation means 72a, an evaluation value calculation means 72b, and a coefficient updating means 72c.

The spectrum calculation means 72a calculates a spectrum Y(t) of the evaluation output signal RIS10 obtained in the evaluation signal obtaining means 71. Here, the spectrum calculation means 72a calculates the spectrum Y(t) from the evaluation output signal RIS10 using one of the known spectrum estimation methods, such as the Fourier transform, maximum entropy method, and the like.

The evaluation value calculation means 72b calculates an evaluation value E(Ci) for the compensation table RT by Formula (2) below using the spectrum Y (t) calculated by the spectrum calculation means 72a.

$$E(c_i) = \sum_t |Y(t)|^M \qquad (2)$$

$E(c_i)$ is the evaluation value for the compensation table of formula (1) above
Y(t) is the spectrum of the evaluation output signal RIS10
M is the set norm set such that the signal component from the reflection body and signal component other than from the reflection body becomes sparse signals in the spectrum Y(t)

It is noted that an evaluation output signal RIS10 is calculated from the compensation table RT using a model coefficient $C_i$, and the Y(t) is obtained by Fourier transforming the evaluation output signal RIS10. Accordingly, the evaluation value E(Ci) in Formula (2) becomes a function of the model coefficient $C_i$.

The coefficient updating means 72c updates the model coefficient $C_i$ such that the evaluation value E(Ci) calculated by the evaluation value calculation means 72b becomes small. It is noted that a setting is made in the optimization means 72c such that the acquisition of the evaluation output signal RIS10, and updating of the evaluation value E (Ci) and model coefficient $C_i$ are repeatedly performed by a preset number k.

Figure 6:
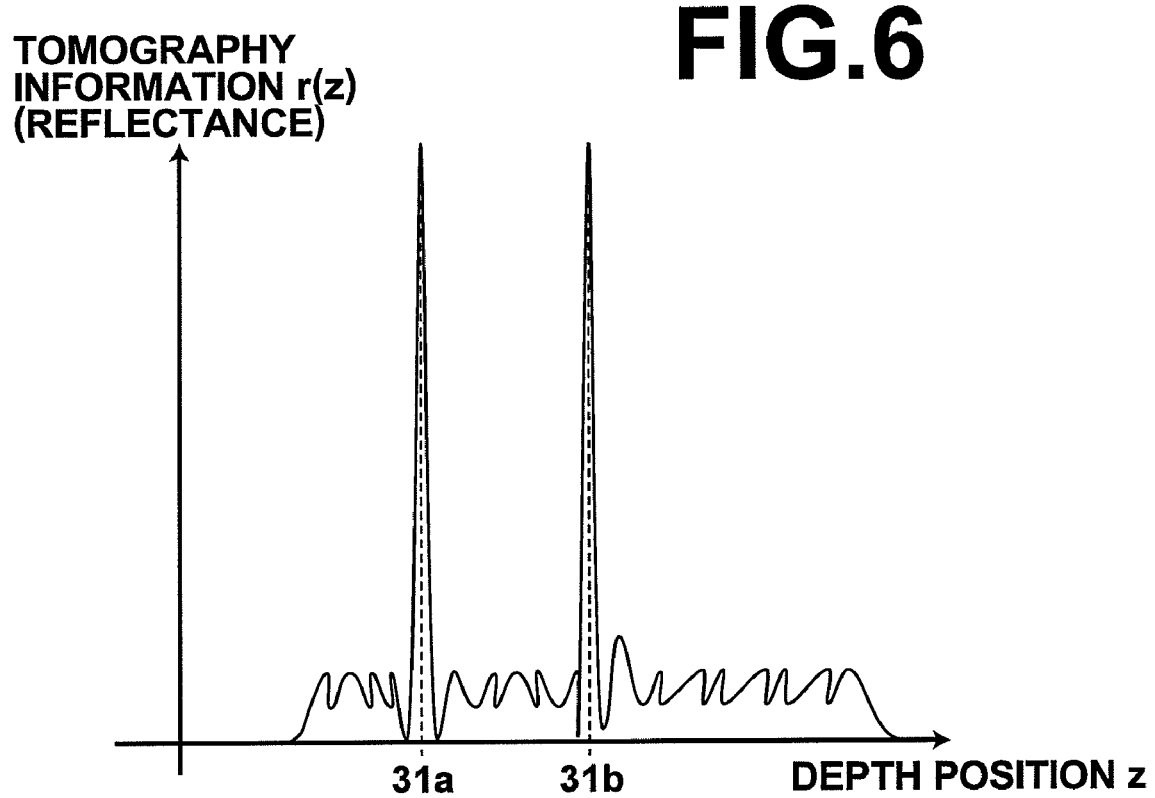
FIG. 6 is a graph illustrating an example spectrum of reflection interference signal calculated in the spectrum calculation means shown in FIG. 4.

Here, the tomography information (reflectance) obtained from the evaluation output signal RIS10 as illustrated in FIG. 6 appears as large values at the inner surface 31a and the outer surface 31b of the sheath 31, and tomography information (reflectance) other than the sheath image appears as very small values. That is, the tomography information r (z) of a reflection body and other tomography information r(z) form a sparse signal.

When the spectrum Y(t) of the evaluation output signal RIS10 is a sparse signal, and the value of the set norm M in Formula (2) is set from 1 to less than 2 (e.g., set norm M=1), the evaluation value E $(C_i)$ becomes small, and a smaller evaluation value E $(C_i)$ means that the spectrum Y(t) is a sparser signal.

However, the tomography information r(z) actually obtained from the reflection body interference signal RIS may sometimes lose sparseness due to wavelength sweeping characteristics of the light source unit 310, light dispersion/absorption characteristics of the measuring object S, wavelength dependent characteristics of various optical parts used in the optical tomography system 1, and the like. If a tomography image P is generated from tomography information r(z) which has lost the sparseness, the image quality is degraded including degraded resolution.

In the mean time, optimization of the model coefficient $C_i$ is performed in the optimization means 72 described above so that the tomography information r(z) obtained from the reflection body interference signal RIS is outputted as a sparse signal. This means that the optimization is performed such that the compensation table RT may compensate for the influence, such as the wavelength sweeping characteristics and the like. Thus, by compensating the interference signal IS using the optimized compensation table RT, image quality degradation may be prevented.

Figure 7:
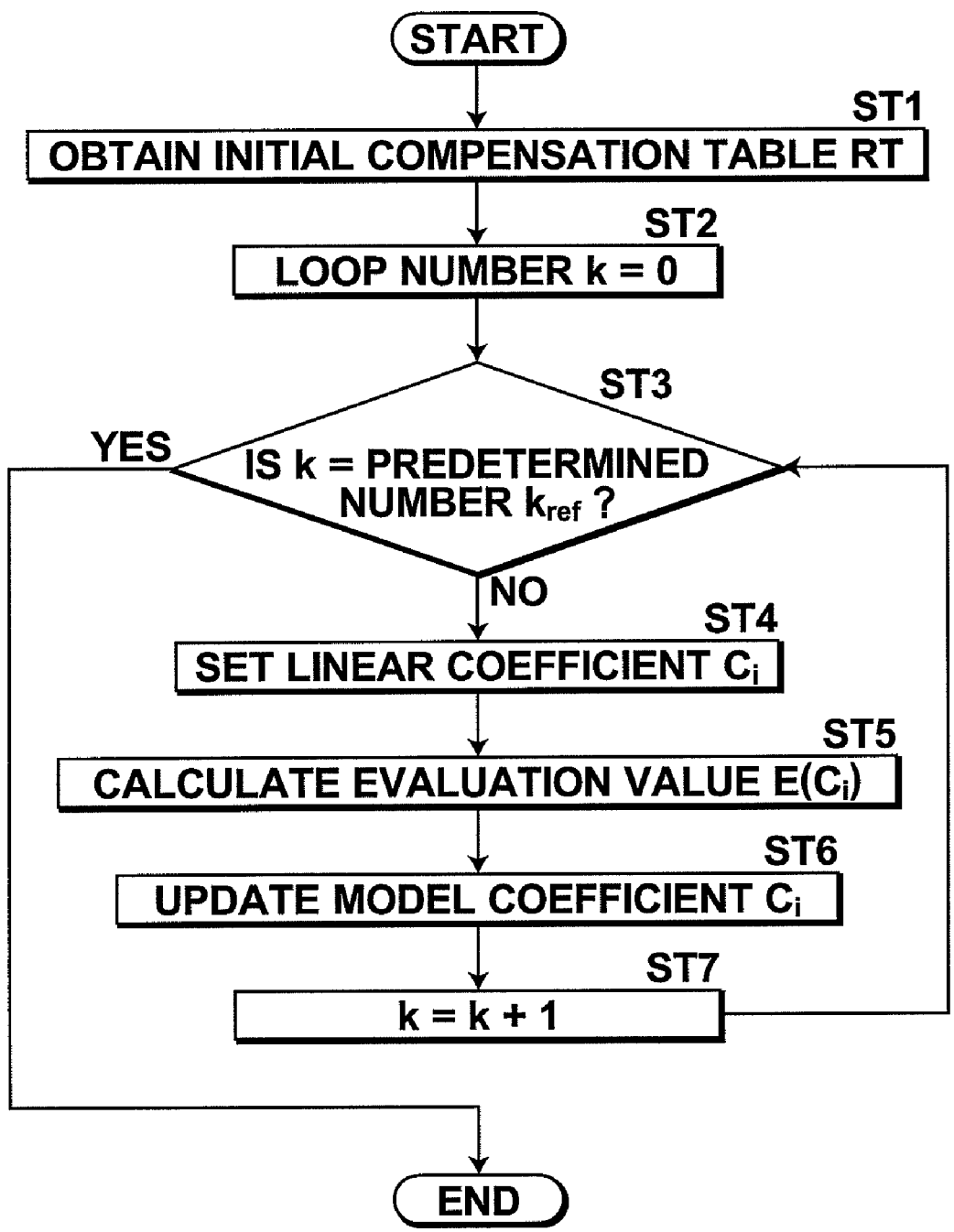
FIG. 7 is a flowchart of an exemplary embodiment of the compensation table generation method of the present invention.

FIG. 7 is a flowchart illustrating an exemplary embodiment of the compensation table generation method of the present invention, and the method will be described with reference to FIG. 7. Hereinafter, a description will be made of a case in which the compensation table RT is not yet generated, and predetermined initial model coefficients C1 to C4 are set as a quartic polynomial (N=4) as in Formula (1') in the optimization means 72 (steps ST1, ST2).

First, when an interference signal IS is obtained in the interference signal obtaining means 51, the interference signal IS is compensated by the initial compensation table RT (Formula (1')) in the optimization means 72, and an evaluation output signal RIS10 is obtained. Next, a spectrum Y(t) of the evaluation output signal RIS10 is calculated in the spectrum calculation means 72a (step ST4), and an evaluation value E $(C_i)$ of the spectrum Y (t) is calculated by the evaluation value calculation means 72b (step ST5). Then, the model coefficient $C_i$ is updated by the coefficient updating means 72c such that the evaluation value $E(C_i)$ becomes small (step ST6). These steps are repeated by a preset number of loops k (steps ST3 to ST7).

As described above, the compensation table RT may be generated easily using the reflection body interference signal RIS, instead of measuring the wavelength sweeping characteristics of the light source unit 310 in advance. That is, in the conventional method, it is necessary to measure the wavelength variation of the light source unit 310 with time. In contrast, by making use of the fact that tomography information obtained by OCT measurement using the optical probe 30 having a reflection body (sheath) forms a sparse signal, the compensation table RT may be generated easily in the compensation table generation unit 70 using Formulae (1) and (2), instead of measuring the wavelength sweeping characteristics of the light source unit in advance. In particular, where the sheath 31 is used as the reflection body, it is not necessary to provide a separate reflection body, such as a mirror, in the optical axis directions z of the measuring light L1, so that the compensation table RT may be generated more easily.

Further, the compensation table is generated using actually obtained reflection body interference signal RIS, so that a compensation table RT in which the light dispersion/absorption characteristics of the measuring object S, wavelength dependent characteristics of various optical parts used in the optical tomography system 1 and the like, as well as the wavelength sweeping characteristics, are taken into account may be generated.

Figure 8:
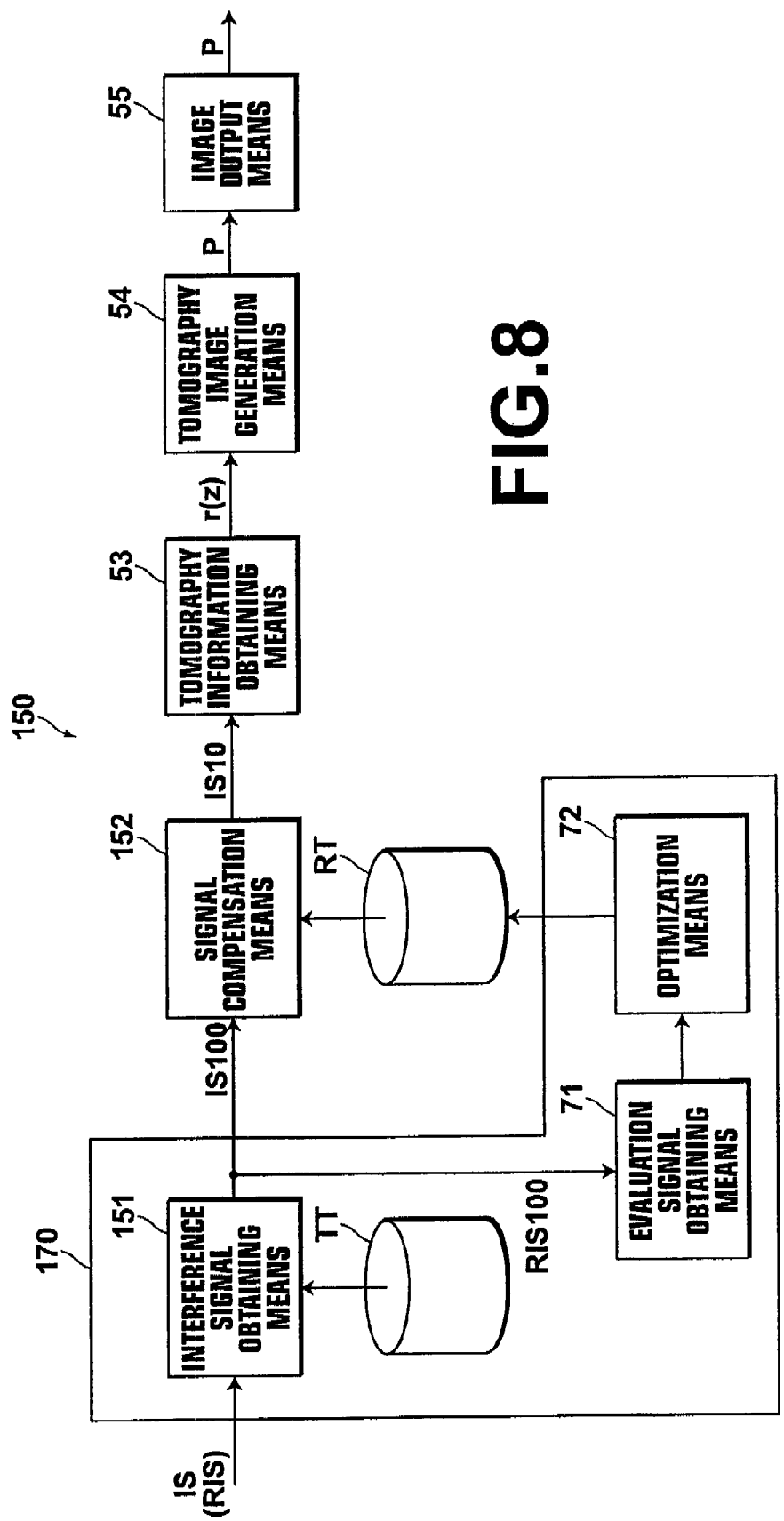
FIG. 8 is a block diagram of another embodiment of the tomography image processing apparatus of the present invention.

FIG. 8 is a block diagram of a tomography image processing apparatus 150 according to another embodiment of the present invention. In the tomography image processing apparatus 150 shown in FIG. 8, components identical to those of the tomography image processing apparatus 50 shown in FIG. 4 are given the same reference numerals and will not elaborated upon further here. The tomography image processing apparatus 150 shown in FIG. 8 differs from the tomography image processing apparatus 50 shown in FIG. 4 in that the interference signal obtaining means 151 has a function to convert the obtained interference signal to an interference signal that indicates interference intensity with respect to each wave number.

The interference signal obtaining means 151 outputs an interference signal IS100 (reflection body interference signal RIS100) obtained by resampling an interference signal IS obtained in the interference light detection means 40 as interference intensities sampled with respect to time axis (wavelength axis) such that the interference intensities are evenly spaced apart on the axis of wave number k using time vs. wavelength sweeping characteristics of the light source unit 310 measured in advance as a conversion table TT. It is noted that the signal conversion method is disclosed in detail in U.S. Pat. No. 5,956,355.

The signal compensation means 152 compensates the interference signal IS100 converted by the interference signal obtaining means 151. In other words, the signal compensation means 152 has a function to finely adjust the conversion result based on the conversion table TT in the interference signal obtaining means 151. The compensation table RT used in the signal compensation means 152 is generated in the compensation table generation unit 170 using the reflection body interference signal RIS100 obtained through signal conversion in the interference signal obtaining means 151. For the optimization of the compensation table RT, the algorithm described above (FIG. 7) may be applied. Also in this case, the compensation table RT may be generated easily, and more finely optimized compensated signal IS100 may be obtained.

According to each of the embodiments described above, when generating a compensation table for compensating an interference signal IS, an interference signal sampled when a reflection body 31 is disposed in the optical axis directions z of the measuring light L1 is obtained as a reflection body interference signal RIS, and model coefficient Ci of the compensation table RT, which is set as a N-order polynomial in Formula (1) above, is optimized using the obtained reflection body interference signal RIS. This eliminates the need for measuring the wavelength sweeping characteristics of the light source unit 310 in advance for generating a compensation table. That is, by making use of the fact that a signal component from the reflection body 31 and a signal component other than the signal component from the reflection body become sparse signals, the compensation table RT may be generated easily.

Further, as shown in FIG. 4, if the optimization means 72 includes: the evaluation signal obtaining means 71 for calculating evaluation output signal RIS 10, which is the compensated reflection body interference signal RIS, using the compensation table RT; spectrum calculation means 72a for calculating a spectrum Y(t) of the evaluation output signal RIS10 obtained in the evaluation signal obtaining means 71; evaluation value calculation means 72b for calculating an evaluation value $E(C_i)$ for the compensation table through Formula (2) using the spectrum Y(t) calculated in the spectrum calculation means 72a; and coefficient updating means 72c for updating the model coefficient $C_i$ such that the evaluation value E(Ci) calculated by the evaluation value calculation means 72b becomes small, the compensation table RT may be generated automatically and efficiently.

Still further, as shown in FIG. 8, the interference signal obtaining means 151 has a function to convert the reflection body interference signal RIS100 representing interference intensity with respect to each wavelength to the reflection body interference signal RIS representing interference intensity with respect to each wave number, and the optimization means 72 is a means for optimizing the model coefficient $C_i$ of the compensation table RT using the reflection body interference signal RIS10 converted by the interference signal obtaining means 151, the interference signal IS100 already converted to the interference intensity with respect to each wave number may be finely adjusted, thereby image quality may be improved.

Further, if the measuring light L1 is guided through the optical probe 30 having the optical fiber FB20 covered by the sheath 31 and irradiated on the measuring object S transmitted through the sheath 31, and a reflection body is the sheath 31, a separate reflection body for obtaining the reflection body interference signal RIS needs not be provided in the optical axis directions z of the measuring light L1, so that the compensation table RT may be generated more easily.

It will be appreciated that the embodiments of the present invention are not limited to those described above. Description has been made of a case in which the sheath 31 is used as the reflection body. But, for example, a mirror may be disposed in the optical axis directions z of the measuring light L1 to make use of the fact that the reflection body tomography information of the mirror and tomography information of other portions form a sparse signal, thereby generating the compensation table RT in the manner as described above.

Further, description has been made of a case in which the reflection body interference signal RIS is obtained with only the sheath 31 being disposed on the optical axis directions z of the measuring light L1. But, the interference signal obtained when the optical probe 30 is inserted into a body cavity and OCT measurement is performed may be used as the reflection body interference signal RIS. That is, the sheath 31 has an extraordinary high reflectance which is not present in ordinary measuring objects, such as a living tissue and the like, so that while the optical probe is inserted, for example, in a body cavity, the sparse relationship between the signal component of the reflection body (sheath) 31 and the signal component of the measuring object S still holds true.

Still further, in the optimization means 72 shown in FIG. 4, description has been made of a case in which the compensation table RT is provided in the form of Formula (1) in which the initial value of the model coefficient $C_i$ is preset. In a case where the table is already stored in a format different from Formula (1), such as a lookup table or the like, the initial value of the model coefficient $C_i$ in Formula (1) may be set from a data string of the lookup table.

Figure 9:
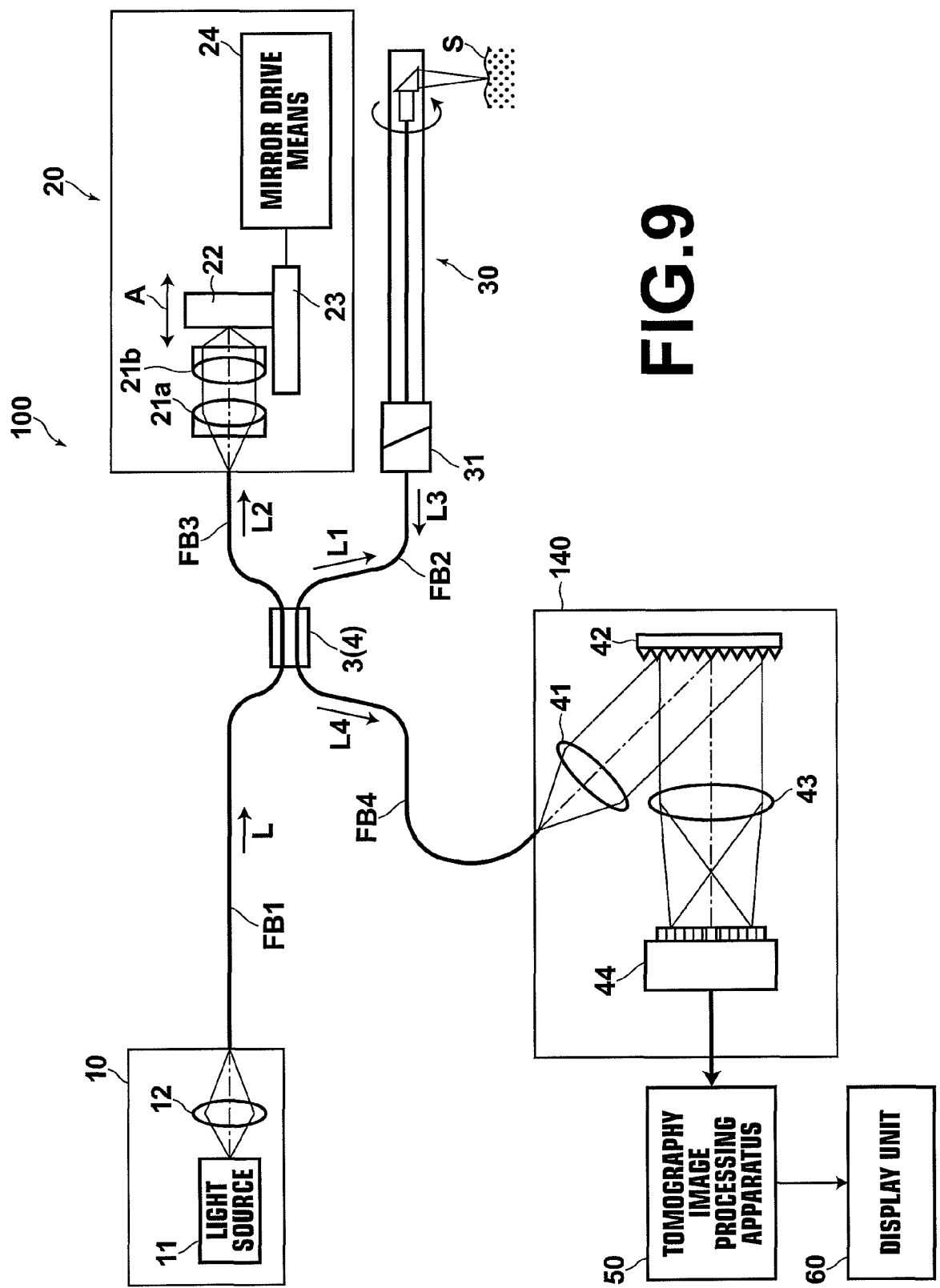
FIG. 9 is a schematic view of another example optical tomography system to which the tomography image processing apparatus of the present invention is applied.

Further, in the embodiment, description has been made of a case in which the tomography image processing apparatus 50 is applied to a so-called SS-OCT measurement. But the apparatus 50 may also be applied to an optical tomography system using SD-OCT measurement like that shown in FIG. 9 in the same way. In FIG. 9, the light source unit 10 is a unit that emits broadband low coherence light. In an interference light detection means 140, interference light L4 is inputted to a diffraction grating 42 through a lens 41, then spectrally separated into respective wavelength ranges by the diffraction grating 42, and detected as an interference signal IS by a light detection section 44 having a plurality of light detection elements (photodiodes or the like) disposed thereon through a lens 43. In this case also, a compensation table RT in which the light dispersion/absorption characteristics of the measuring object S, wavelength dependent characteristics of various optical parts used in the optical tomography system 1 and the like are taken into account may be generated easily.

What is claimed is:

1. A compensation table generation method for generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the method comprising the steps of:
  obtaining an interference signal sampled when a reflection body is disposed in the optical axis directions of the measuring light as a reflection body interference signal;
  calculating, using at least one central processing unit, an evaluation output signal by resampling the obtained reflection body interference signal in a sampling space converted by Formula (1) below; and
  optimizing, using at least one central processing unit, a model coefficient of a compensation table set as a N-order polynomial in Formula (1) below using the calculated evaluation output signal $$y = \sum_{i=1}^{N-1} c_i x^{N+1-i} + \left(1 - \sum_{i=1}^{N-1} c_i\right) x \qquad (1)$$

x is the reflection body interference signal sampling space
y is the evaluation output signal sampling space
$c_i$ is the model coefficient (i=1, 2, . . . , N−1).

2. The non-transitory compensation table generation method according to claim 1, wherein the optimizing the model coefficient is performed without previously measuring a relationship between the time change of a wavelength sweep and a wave number.

3. A compensation table generation apparatus for generating a compensation table for compensating an interference signal obtained by emitting light, splitting the emitted light into measuring light and reference light, combining reflection light from a measuring object when the measuring light is irradiated on the measuring object with the reference light, and sampling interference light when the reflection light is combined with the reference light as the interference signal, the apparatus comprising:
  an interference signal obtaining means for obtaining an interference signal sampled when a reflection body is disposed in the optical axis directions of the measuring light as a reflection body interference signal;
  an evaluation signal calculation means for calculating, using at least one central processing unit, an evaluation output signal by resampling the reflection body interference signal obtained in the interference signal obtaining means in a sampling space converted by Formula (1) below; and
  an optimization means for optimizing, sing at least one central processing unit, a model coefficient of a compensation table set as a N-order polynomial in Formula (1) below using the evaluation output signal calculated by the evaluation signal calculation means $$y = \sum_{i=1}^{N-1} c_i x^{N+1-i} + \left(1 - \sum_{i=1}^{N-1} c_i\right) x \qquad (1)$$

x is the reflection body interference signal sampling space
y is the evaluation output signal sampling space
$c_i$ is the model coefficient (i=1, 2, . . . , N−1).

4. The compensation table generation apparatus according to claim 3, wherein the optimization means includes:
  a spectrum calculation means for calculating a spectrum of the evaluation output signal obtained in the evaluation signal calculation means;
  an evaluation value calculation means for calculating an evaluation value for the compensation table by Formula (2) below using the spectrum calculated in the spectrum calculation means; and
  a coefficient updating means for updating the model coefficient such that the evaluation value calculated by the evaluation value calculation means becomes small $$E(c_i) = \sum_t |Y(t)|^M \qquad (2)$$

$E(c_i)$ is the evaluation value for the compensation table of formula (1) above
Y(t) is the spectrum of the evaluation output signal
M is the set norm set such that the signal component from the reflection body and signal component other than from the reflection body become sparse signals in the spectrum Y(t).

5. The compensation table generation apparatus according to claim 4, wherein the value of the set norm is from 1 to less than 2.

6. The compensation table generation apparatus according to claim 3, wherein the optimization means is a means for optimizing the model coefficient by simplex method.

7. The compensation table generation apparatus according to claim 3, wherein:
  the interference signal obtaining means is a means for obtaining a reflection body interference signal whose sampling space is the wavelength of the interference light; and
  the evaluation signal calculation means is a means for calculating an evaluation output signal whose sampling space is the wave number of the interference light by resampling the reflection body interference signal in the sampling space converted by Formula (1).

8. The compensation table generation apparatus according to claim 3, wherein:
  the interference signal obtaining means is a means having a function to covert a reflection body interference signal representing the interference intensity with respect to the wavelength of the interference light to a reflection body interference signal representing the interference intensity with respect to the wave number of the interference light; and the evaluation signal calculation means is a means for calculating an evaluation output signal by resampling the reflection body interference signal representing the interference intensity with respect to the wave number obtained by the interference signal obtaining means in the sampling space converted by Formula (1).

9. The compensation table generation apparatus according to claim 3, wherein the measuring light is light guided through an optical probe having an optical fiber covered by a sheath and irradiated on the measuring object transmitted through the sheath, and the reflection body is the sheath.

10. The compensation table generation apparatus according to claim 3, wherein the optimization means optimizes the model coefficient without previously measuring a relationship between the time change of a wavelength sweep and a wave number.

11. A non-transitory compensation table generation computer program product for generating a compensation table for compensating an interference signal obtained by emitting light, splitting the emitted light into measuring light and reference light, combining reflection light from a measuring object when the measuring light is irradiated on the measuring object with the reference light, sampling interference light when the reflection light is combined with the reference light as the interference signal, the program product causing a computer to perform the steps of:

obtaining an interference signal sampled when a reflection body is disposed in the optical axis directions of the measuring light as a reflection body interference signal;

calculating an evaluation output signal by resampling the obtained reflection body interference signal in a sampling space converted by Formula (1) below; and optimizing a model coefficient of a compensation table set as a N-order polynomial in Formula (1) below, using the calculated evaluation output signal $$y = \sum_{i=1}^{N-1} c_i x^{N+1-i} + \left(1 - \sum_{i=1}^{N-1} c_i\right) x \quad (1)$$

x is the reflection body interference signal sampling space
y is the evaluation output signal sampling space
$c_i$ is the model coefficient (i=1, 2, ..., N−1).

12. The compensation table generation computer program product according to claim 11, wherein the optimizing the model coefficient is performed without previously measuring a relationship between the time change of a wavelength sweep and a wave number.

13. A tomography image processing apparatus for generating a tomography image of a measuring object by emitting light, splitting the emitted light into measuring light and reference light, combining reflection light from the measuring object when the measuring light is irradiated on the measuring object with the reference light, sampling interference light when the reflection light is combined with the reference light as an interference signal, and obtaining tomography information of the measuring object using the interference signal, the apparatus comprising:

an interference signal obtaining means for obtaining an interference signal;

an evaluation signal calculation means for calculating, using at least one central processing unit, an evaluation output signal by resampling a reflection body interference signal, which is a portion of the interference signal obtained in the interference signal obtaining means, in a sampling space converted by Formula (1) below;

an optimization means for optimizing, sing at least one central processing unit, a model coefficient of a compensation table set as a N-order polynomial in Formula (1) below, using the evaluation output signal calculated by the evaluation signal calculation means;

a signal compensation means for compensating the interference signal obtained in the interference signal obtaining means using the compensation table optimized by the optimization means;

a tomography information obtaining means for obtaining tomography information of the measuring object using the interference signal compensated by the signal compensation means; and a tomography image generation means for generating a tomography image using the tomography information obtained by the tomography information obtaining means $$y = \sum_{i=1}^{N-1} c_i x^{N+1-i} + \left(1 - \sum_{i=1}^{N-1} c_i\right) x \quad (1)$$

x is the reflection body interference signal sampling space
y is the evaluation output signal sampling space
$c_i$ is the model coefficient (i=1, 2, ..., N−1).

14. The tomography image processing apparatus according to claim 13, wherein the optimization means optimizes the model coefficient without previously measuring a relationship between the time change of a wavelength sweep and a wave number.

* * * * *